United States Patent
Savich

[11] 3,939,240
[45] Feb. 17, 1976

[54] METHOD FOR FORMING FIBROUS PADS
[75] Inventor: Peter P. Savich, Longmeadow, Mass.
[73] Assignee: Scott Paper Company, Philadelphia, Pa.
[22] Filed: May 16, 1974
[21] Appl. No.: 470,548

[52] U.S. Cl. .................... 264/91; 264/89; 264/93; 264/109; 264/119; 264/120; 264/121; 264/335
[51] Int. Cl.² .......................................... D04H 1/00
[58] Field of Search .......... 156/62.2, 62.4; 425/437, 425/455, 80, 82; 19/155, 148; 264/88, DIG. 78, 89, 90, 91, 113, 109, 121, 120, 93, 101, 112, 119, 335

[56] References Cited
UNITED STATES PATENTS

| | | | |
|---|---|---|---|
| 2,073,329 | 3/1937 | Winter | 264/112 |
| 3,352,954 | 11/1967 | Smith | 264/91 |
| 3,766,922 | 10/1973 | Krusko | 128/284 |

*Primary Examiner*—Willard E. Hoag
*Attorney, Agent, or Firm*—Martin L. Faigus; William J. Foley

[57] ABSTRACT

Method for the dry forming of fibrous pads employ a pad forming member closing the lower end of a pad forming area. The pad forming member preferably is in the form of a condenser roll having three-dimensional pockets, or cavities about the periphery thereof. Each cavity includes an opening into it, and the cavities are brought into communication with the pad forming area as the condenser roll is continuously driven during operation of the apparatus. Each cavity is defined by foraminous bottom and side surfaces, the surface area of which is greater than the surface area of the opening into it. An air suspension of fibers is formed in the pad forming area, and a vacuum is applied through the foraminous surfaces of each cavity when it is disposed in the pad forming area to pull the air of the suspension through the foraminous surfaces, and deposit the fibers carried in the air suspension onto the foraminous surfaces in the form of a fibrous layer. A transfer conveyer is fed in overlying relationship with the opening of each cavity downstream of the pad forming area, and a vacuum is applied through the transfer conveyer to transfer the fibrous layer from each cavity onto the transfer conveyer. The fibers deposited on the transfer conveyer are confined to an area substantially equal to the surface area of the opening into each cavity, and accordingly, the fibers are consolidated as they are transferred from each cavity onto the transfer conveyer to form fibrous pads having a greater basis weight than the basis weight of the fibrous layers formed within the cavities.

2 Claims, 9 Drawing Figures

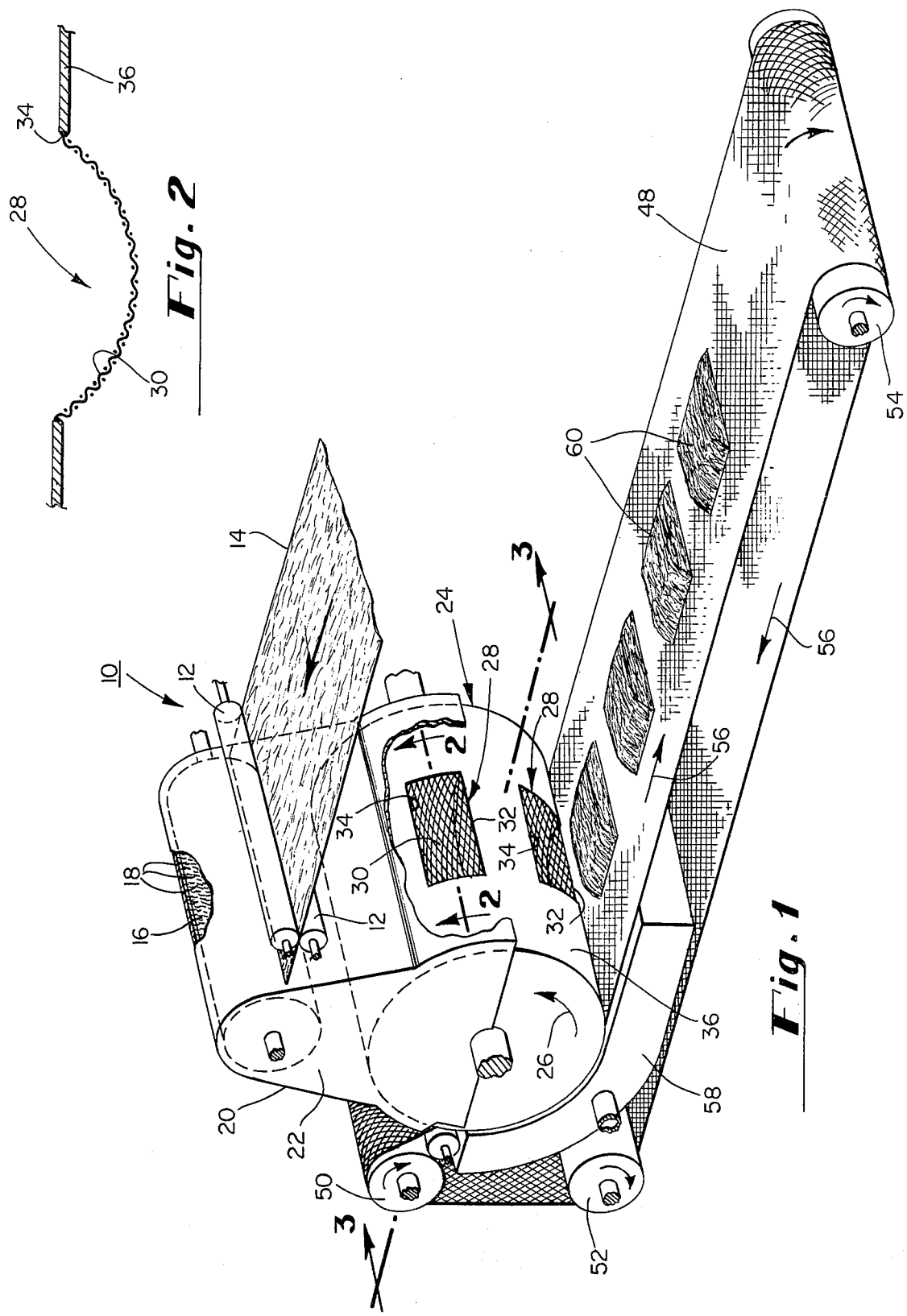

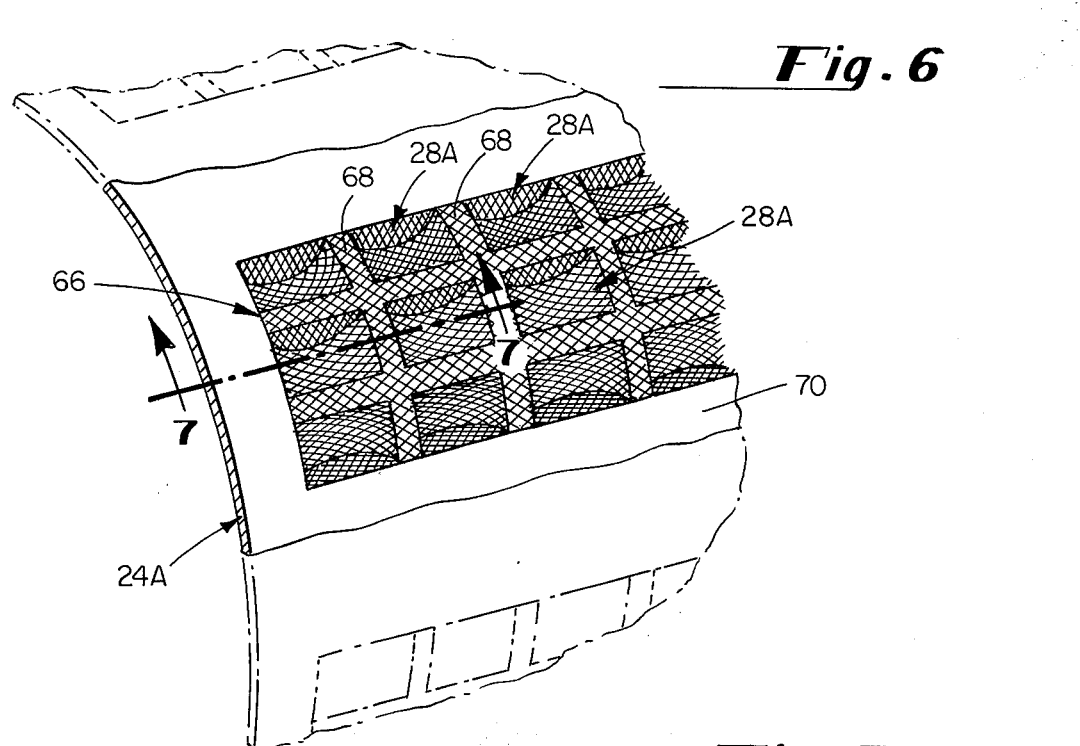
*Fig. 6*
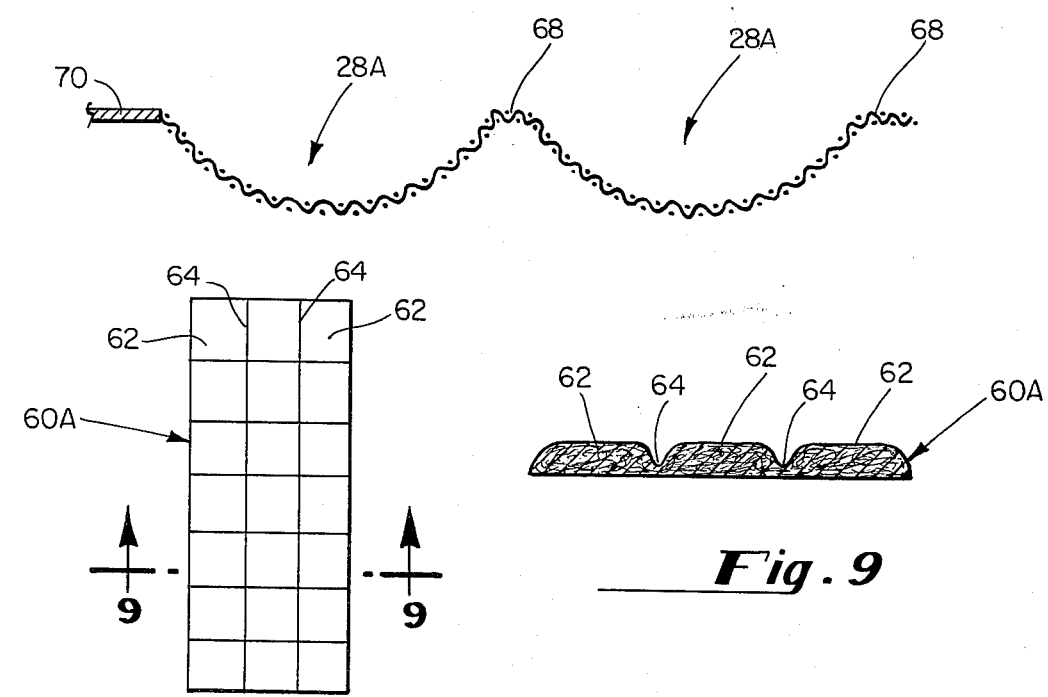
*Fig. 7*
*Fig. 8*
*Fig. 9*

METHOD FOR FORMING FIBROUS PADS

BACKGROUND OF THE INVENTION

1. Field of the Invention

This invention relates to an apparatus and method for dry forming fibrous pads, and specifically, to apparatus and method for forming fibrous pads suitable for use by themselves, or in conjunction with other components to form sanitary products such as disposable diapers, sanitary napkins and the like.

2. Description of the Prior Art

Apparatus and method for forming absorbent fibrous pads are known in the prior art. Such fibrous pads are often formed from 100% woodpulp fibers, and are utilized as internal absorbent components in sanitary products such as disposable diapers, sanitary napkins and the like. In many of these applications the fibrous pads are required to have a relatively high basis weight. For example, the center region of the absorbent pad shown in FIG. 3 of U.S. Pat. No. 3,766,922 issued on Oct. 23, 1973, and assigned to Scott Paper Company, has a basis weight of approximately 45 oz/yd.$^2$.

It has been suggested to dry form fibrous pads directly into three-dimensional pockets, or cavities of pad forming members which close the lower end of a pad forming area in conventional dry forming equipment. The pad forming member can be in the form of a cylindrical condenser roll having a three-dimensional pocket formed therein, or alternatively, can be in the form of a foraminous belt having three-dimensional pockets formed therein. In these prior art apparatus the fibrous pads are directly formed into the pockets by applying a vacuum through only the lower, or bottom surface of the pockets, i.e., only the bottom surface is foraminous. When the pad forming member is in the form of a cylindrical condenser roll the side walls of each three-dimensional pocket converge toward each other in a direction from the outer periphery of the condenser roll to the bottom surface, and accordingly, the surface area of the bottom surface of each pocket is less than the surface area of the opening into it.

In other prior art apparatus and methods fibrous pads are directly formed on a cavity-free outer foraminous surface of a cylindrical condenser roll or foraminous belt.

Accordingly, in the prior art apparatus and methods the foraminous surface through which the vacuum is applied either has substantially the same area (the outer surface of a condenser roll or belt), or a lesser area (the bottom surface of a pocket in a condenser roll) than the area of the fibrous pad which ultimately is to be formed.

When fibers are initially deposited as a layer on a foraminous surface from an air suspension they establish increased resistance to air flow through said surface. This resistance to air flow increases significantly with slight increases in basis weight of the fibrous layer formed on the foraminous surface. This resistance to air flow can become so great as to prevent the required volume of air containing suspended fibers to be pulled through the foraminous surface to form a fibrous pad having a desired basis weight. Even the use of uneconomical, high horsepower vacuum pumps to establish high vacuum levels may not solve the problem, since the high vacuum levels may merely consolidate the fibers into an air-impervious layer on the foraminous surface before the requisite weight of fibers is deposited in said cavity. When the vacuum level is adjusted to avoid excessive compaction of the fibrous layer the large resistance to air flow through the layer still makes it necessary to employ a long formation area to form fibrous pads of a high basis weight. Accordingly, excessively large equipment taking up valuable plant space may be required. The instant invention overcomes the problems set forth in this paragraph.

SUMMARY OF THE INVENTION

The method and apparatus of this invention resides in initially forming a fibrous layer on foraminous surfaces of a three-dimensional pocket or cavity having a greater surface area than the area of a fibrous pad which is to be formed therefrom. The critical feature of the method and apparatus of this invention is that the surface area of the foraminous surfaces of each cavity is greater than the area of the opening into it. Accordingly, a predetermined total weight of fibers can be deposited on the foraminous portions of the cavity in the form of a fibrous layer incompletely filling the cavity, and having a lower basis weight (weight/unit area) than can be deposited on a surface having the same or lesser area than the cavity opening. Since the pressure drop which has to be established through a foraminous surface to direct a gas therethrough increases with increased basis weight of a fibrous layer thereon, a lesser pressure drop has to be established through the foraminous surfaces defining each cavity to deposit a predetermined total weight of fibers therein, than would have to be established if the same total weight of fibers were deposited on a foraminous surface of substantially the same, or lesser area than the area of the cavity opening.

After the fibrous layer is formed within each cavity, means are provided to transfer allegiance of the layer to a transfer conveyer which is directed in overlying contacting relationship with the forming member so as to overlie the opening into each cavity. In the preferred embodiment of the invention the transfer conveyer is foraminous and a vacuum is applied therethrough to transfer allegiance of the fibrous layer from each cavity to the transfer conveyer to thereby form the fibrous pads on said transfer conveyer. The fibrous pads have a greater basis weight than the fibrous layers from which they are formed. This results from the consolidation of the fibrous layers into a smaller area on the transfer conveyer than they occupied within the cavities. To further explain, the fibrous layer from each cavity is transferred to the transfer conveyer over an area substantially equal to the area of the opening into the cavity. The area of the cavity opening is less than the foraminous surface area of the cavity defined by the base and side surfaces thereof. Accordingly, the fibrous layer is confined to a lesser area on the transfer conveyer than it occupied in the cavity; thereby resulting in the formation of a pad which has a greater basis weight than the fibrous layer formed in the cavity. Therefore, this invention permits the formation of a fibrous layer having a lower basis weight than a fibrous pad which ultimately is to be formed, and accordingly permits the use of low cost, low horsepower vacuum sources to form such a fibrous pad and/or the use of reasonably sized equipment which does not take up excessive plant space.

Further objects and advantages of this invention will become apparent upon reading the detailed description which follows taken in conjunction with the drawings.

BRIEF DESCRIPTION OF THE DRAWINGS

FIG. 1 is a schematic isometric view of an apparatus according to this invention;

FIG. 2 is a sectional view taken along line 2—2 of FIG. 1;

FIG. 6 is an isometric view showing a part of a pad forming member according to an alternative embodiment of this invention;

FIG. 7 is a sectional view taken along line 7—7 of FIG. 6;

FIG. 8 is a plan view of a fibrous pad formed by employing the pad forming member shown in FIG. 6; and FIG. 9 is a sectional view taken along line 9—9 of FIG. 8.

DESCRIPTION OF THE PREFERRED EMBODIMENTS OF THE INVENTION

Figure 3:
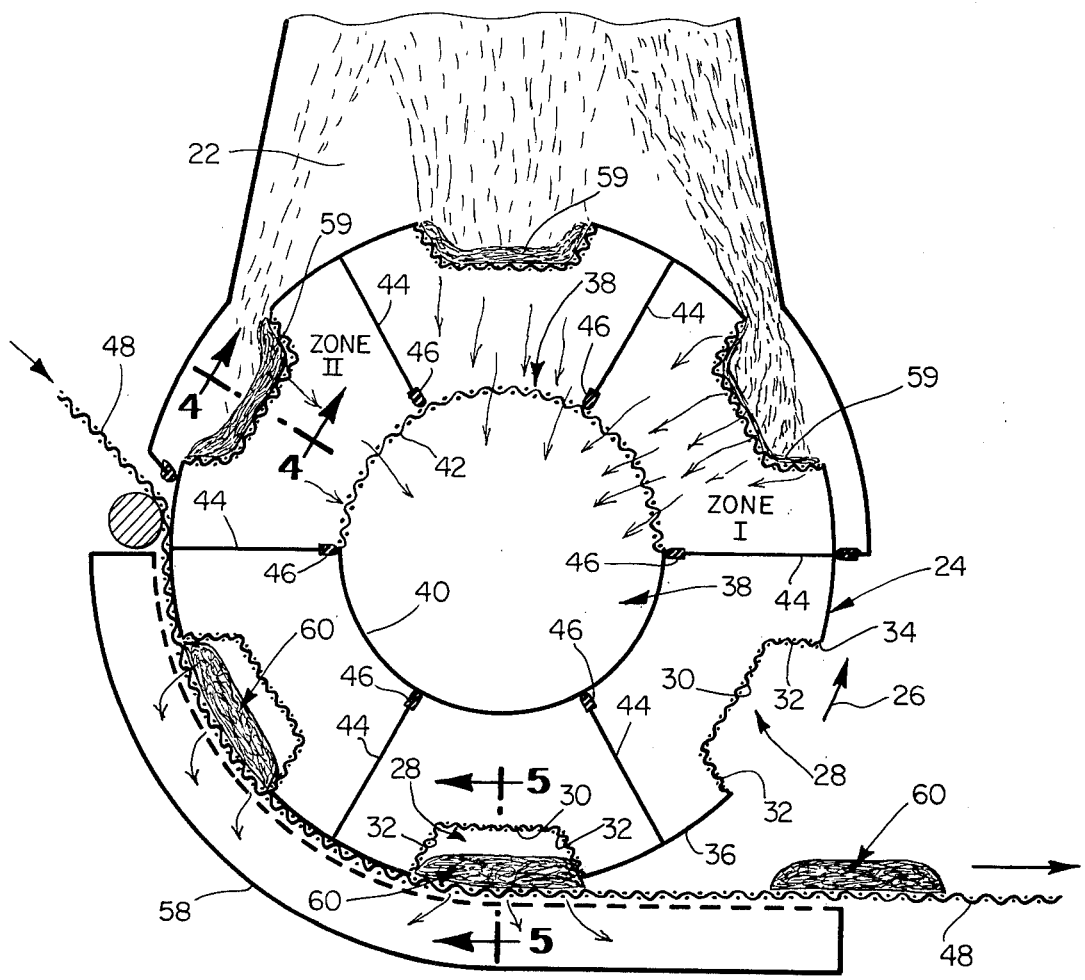
FIG. 3 is a sectional view taken along line 3—3 of FIG. 1.

Referring to FIG. 1, the apparatus 10 for manufacturing dry formed fibrous pads 60 includes feed rolls 12 for directing a fibrous feed mat 14 into engagement with a fiberizing roll 16. The fiberizing roll 16 includes surface clothing including pins or teeth 18 projecting therefrom. A shroud 20 encloses the fiberizing roll 16 to define a pad forming area 22. The pad forming area is closed at its lower end by a pad forming member in the form of a cylindrical condenser roll 24 which is driven by suitable drive means (not shown) in the direction indicated by arrow 26 (FIGS. 1 and 3). The above-described structural features, or equivalents thereof, are conventional in many prior art apparatus for forming dry formed fibrous webs or pads. For example, the Rando-Webber manufactured by Curlator Corporation of Rochester, N.Y., employs similar structural elements which can be utilized in this invention.

Referring to FIGS. 1 - 3, unique structural features of the condenser roll 24 of this invention will be described. The condenser roll 24 includes a plurality of three-dimensional pockets, or cavities 28 uniformly spaced about the periphery thereof. The number of cavities 28 can be varied depending upon the size of the roll, and the number of pads which one desires to form. In the embodiment shown in this invention the roll contains six cavities.

Each cavity 28 includes a foraminous, concave base 30 providing the bottom region and part of the side region of the cavity (FIG. 2). The cavities 28 additionally include foraminous side surfaces 32 joined to the concave base 30 and diverging outwardly therefrom to complete the cavity construction (FIGS. 1 and 3). The upper margins of each cavity terminate substantially in alignment with the outer periphery of the condenser roll, and define an opening 34. In the embodiment shown in FIGS. 1 - 3 the outer periphery of the condenser roll 24 is air-impervious.

A critical feature of this invention is that the foraminous surface area of each cavity 28 provided by the foraminous concave base 30 and the side surfaces 32 is greater than the area of the cavity opening 34 bound by the upper margins of each of said cavities 28. The importance of this feature will be explained later in the application.

Referring to FIG. 3, a cylindrical vacuum chamber 38 is mounted within the interior of the condenser roll 24, and is secured to fixed framework (not shown) to prevent rotation thereof. The cylindrical vacuum chamber 38 is connected to a suitable source of vacuum, such as the low pressure side of a fan (not shown). A lower hemispherical portion 40 of the vacuum chamber 38 is either constructed of an air-impervious member, or coated with a suitable material to render it air-impervious. The upper hemispherical portion 42 is air-pervious. A plurality of partitions 44 are fixedly connected to the outer shell of the condenser roll 24, and each partition has a sealing bushing 46 which is maintained in frictional, sliding engagement with the outer surface of the vacuum chamber 38. The partitions are connected to the condenser roll 24 intermediate adjacent cavities 28.

Referring to FIGS. 1 and 3, a foraminous transfer conveyer 48 is trained about a plurality of mounting rolls 50, 52 and 54, respectively. Any number of rolls can be utilized; however, the rolls should be arranged so that the transfer conveyer 48 is mounted in partial wrapping engagement with the condenser roll 24 downstream of the pad forming area 22. One or more of the transfer conveyer mounting rolls is positively driven to drive the transfer conveyer 48 in the direction indicated by arrows 56. A transfer vacuum box 58 is positioned beneath the upper run of the transfer conveyer 48 underlying the region of the upper run which is in wrapping engagement with the condenser roll 24. A partial vacuum is established through the vacuum box 58 by any conventional source of vacuum, such as a fan (not shown).

Referring to FIGS. 1 and 3, the operation of the apparatus 10 of this invention will be described. The feed mat 14 is directed into engagement with the fiberizing roll 16 by the feed rolls 12. The fiberizing roll is rotatably driven at a high speed to separate fibers from the feed mat 14 and direct them into the pad forming area 22 to form an air suspension of substantially individualized fibers within said pad forming area. A partial vacuum is established through the cylindrical vacuum chamber 38 as the condenser roll 24 is moved in the direction indicated by arrow 26. As a cavity 28 enters the forming area (Zone I - FIG. 3) it is in alignment with the foraminous region 42 of the vacuum chamber 38. Accordingly, the vacuum applied through the vacuum chamber 38 establishes a pressure drop across the foraminous base 30 and side surfaces 32 of the cavity 28. This pressure drop is effective to pull the air of the suspension through the cavity, and to deposit fibers in the suspension in the pocket in the form of a fibrous layer 59. As the cavity continuously travels through the pad forming area 22 the fibers continuously build up in the layer 59 until complete formation of the layer 59 is establishes at Zone II.

Figure 4:
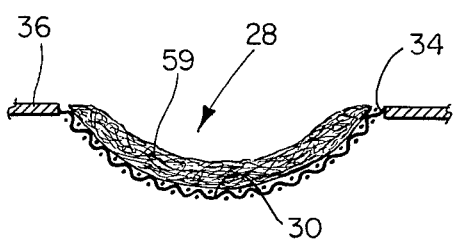
FIG. 4 is a sectional view taken along line 4—4 of FIG. 3.

Referring to FIGS. 3 and 4, the foraminous layer 59 is deposited over substantially the entire foraminous region of the cavity 28 and incompletely fills said cavity. As explained earlier in this application, the surface area of the foraminous portion of each cavity 28 is greater than the area of the cavity opening 34. Accordingly, a predetermined total weight of fibers can be deposited on the foraminous portions of the cavity with a lower basis weight (weight/unit area) than can be deposited on a foraminous surface of a lesser area, such as by depositing the fibers on a region of the outer surface of the condenser roll 24 corresponding in area to that of the cavity opening 34. Since the pressure drop which has to be established through a foraminous surface to direct air therethrough increases with increased basis weight of a fibrous web or layer thereon, a lesser pressure drop has to be established through the foraminous surfaces defining cavities 28 to deposit a predetermined total weight of fibers therein, than would have to be established if the same total weight of fibers were deposited on a foraminous surface of a lesser area.

Figure 5:
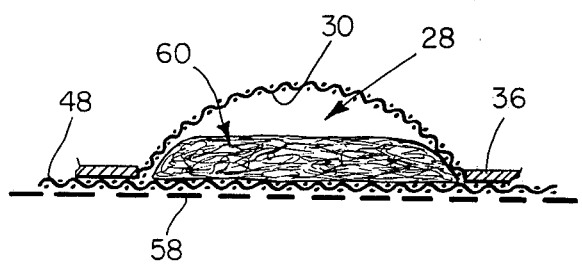
FIG. 5 is a sectional view taken along line 5—5 of FIG. 3.

As a cavity 28 leaves Zone II (FIG. 3) of the forming area, the upper run of transfer conveyer 48 is moved into engagement with the outer periphery of the condenser roll 24 in overlying relationship with the cavity opening 34. Also, the cavity 28 is in alignment with masked portion 40 of the cylindrical vacuum chamber 38 so that the partial vacuum which is established through the vacuum chamber 38 is ineffective to retain the fibrous layer 59 within the pocket. In this same location the pocket opening 34 is in overlying relationship with the transfer vacuum box 58, through which a partial vacuum is established. This partial vacuum is effective to transfer allegiance of the fibrous layer 59 from the pocket 28 to the transfer conveyer 48 to thereby form a fibrous pad 60 (FIGS. 3 and 5).

The fibrous pad 60 has a greater basis weight than the fibrous layer 59 from which it is formed. This results from the consolidation of the fibrous layer 59 into a smaller area on the transfer conveyer 48 than it occupied within the cavity 28. To further explain, the fibrous layer 59 from the pocket 28 is transferred to the transfer conveyer 48 over an area substantially equal to the area of the pocket opening 34. The area of the cavity opening 34 is less than the foraminous area of the cavity 28 defined by the base 30 and side surfaces 32. Accordingly, the fibrous layer 59 is confined to a lesser area on the transfer conveyer 48 than it occupied in the cavity 28; thereby resulting in the formation of a pad which has a greater basis weight than the fibrous layer 59 formed in the cavity 28.

Since the partial vacuum established through each cavity 28 is established through the entire area upon which the fibrous layer 59 is formed, the method and apparatus of this invention permits the formation of high basis weight fibrous pad 60 with the use of less costly, lower horsepower vacuum sources than can be utilized in the prior art apparatus and methods. To further explain, the present invention permits the formation of a fibrous pad 60 of a given basis weight by utilizing a vacuum source which need only be capable of establishing a partial vacuum of a sufficient level to form a fibrous layer 59 having a lower basis weight. The lower basis weight of the fibrous layer 59 within each cavity 28 establishes a lower resistance to air flow through the foraminous surfaces and fibrous layer 59 within each cavity 28 than would be established if the fibrous layer 59 were formed on a foraminous surface having less surface area than the area of the foraminous surfaces of the cavity 28. This lower resistance to air flow permits the use of lower horsepower vacuum sources to achieve the final formation of the fibrous layer 59 in the method and apparatus of this invention.

The formed fibrous pads 60 (FIGS. 3 and 5) are maintained in engagement with the transfer conveyer 48 as the condenser roll 24 separates from the pads by maintaining the application of a partial vacuum through the transfer vacuum box 58 at the time of separation.

The formed pad 60 is conveyed by the transfer conveyer 48 to subsequent processing equipment (not shown) downstream of the apparatus 10. For example, such subsequent equipment can include converting equipment for encasing the fibrous pad 60 between a fluid pervious facing layer and a fluid impervious (e.g. plastic) backing layer to form a disposable diaper or sanitary napkin.

Referring to FIGS. 6 and 7, an alternative construction of a condenser roll 24A is shown for forming fibrous pads 60A (FIGS. 8 and 9) having high basis weight regions 62 and low basis weight regions 64 therein. Each fibrous pad 60A is formed on a region 66 of the condenser roll 24A which comprises a plurality of closely spaced cavities 28A separated by foraminous corridor regions 68. In all other respects the apparatus is substantially identical to that disclosed in FIG. 1. The low basis weight regions 64 of the fibrous pad 60A correspond to the regions of the fibrous layer formed on the foraminous corridors 68, and the high basis weight regions 62 correspond to the regions of the fibrous layer formed within the cavities 28A. The fibers deposited on the corridors 68 (i.e., substantially planar regions) will build up to substantially the same level or height as the fibers deposited within the three-dimensional cavities 28A. However, due to the fact that the foraminous surface area of each cavity 28A is greater than the area of the opening into it, transfer of the fibrous layers from the cavities 28A onto the transfer conveyer 48 will result in the formation of higher basis weight pad areas 62 than that of the fibrous layer within each cavity 28A. However, the fibrous layers deposited on the corridor regions 68 will be transferred to the transfer conveyer over substantially the same area as the corridor area, and accordingly, substantially no increase in basis weight will take place in these regions. In this manner a pad having varying basis weights can be formed.

A pad having different basis weight regions can also be formed by grouping cavities together having foraminous surfaces of differency surface areas. When the fibrous layers formed in such a grouping of cavities is transferred to a transfer conveyer, the basis weight in different sections of the pad will vary in relationship to the surface areas of the cavities from which the sections of the pad were formed.

Although certain preferred embodiments of this invention have been disclosed; other modifications can exist. For example, the outer periphery of the forming member 24 (FIG. 1) which surrounds each cavity 28 can be completely foraminous. In such an embodiment, the fibrous pads 60 which are formed from the fibrous layers 59 within each cavity 28 will be integrally joined with fibrous web sections of a lower basis weight which are initiailly formed as layers on the foraminous outer peripheral regions of the condenser roll surrounding the cavities. This same modification can exist with respect to the forming member 24A disclosed in FIGS. 6 and 7. Reference throughout this application, including the claims, to the formation of fibrous pads includes the formation of alternative web constructions as set forth in this paragraph.

The fibrous feed mat 14 preferably is formed of woodpulp fibers having an average fiber length less than one-fourth inch. However, it is within the scope of this invention to form fibrous feed mats from any type of fibers, including blends of woodpulp fibers and longer textile-length fibers. For example, the fibrous feed mat 14 can include over 75% by weight woodpulp fibers with the remainder of the fibers being longer textile-length fibers, such as rayon, polyester, cotton, etc.

An illustrative example indicating the advantages which can be achieved according to the method of this invention will now be described. This example is not intended to limit the broadest aspects of the invention, but is intended to illustrate the dramatic results which can be achieved by practicing the invention.

A cavity was formed in which the foraminous forming surface had an increase in surface area of 70% as compared to the area of the opening into the cavity defined by the upper margins thereof. Accordingly, if one desired to form a fibrous pad 60 having a basis weight of 23.3 oz./yd.$^2$, it would only be necessary to form a fibrous layer 59 in the pocket having a basis weight of 13.7 (i.e., 23.3/1.7). If the cavity of this invention were not employed, and the fibrous pad were to be formed on a surface having an area equal to the cavity opening defined by the upper margins thereof, the total basis weight of 23.3 oz./yd.$^2$ would have to be formed on this surface. A pressure drop of approximately 80 inches of water would have to be established to form a fibrous pad or layer having a basis weight of 23.3 oz./yd.$^2$ when an air suspension of fibres approaches the forming surface at 1550 feet per minute. However, at this same approach velocity (1550 feet per minute), a pressure drop of less than 48 inches of water would have to be established to form the 13.7 oz./yd.$^2$ fibrous layer within the cavity. Accordingly, the pressure drop requirement is greatly reduced to form a fibrous pad of a given basis weight by employing applicant's invention, as opposed to directly forming the pad of the desired basis weight on an upper foraminous surface having an area equal to that of the cavity opening defined by the upper margins of the cavity. Since a lower pressure drop is required, lower horsepower, less costly vacuum equipment can be utilized, or alternatively, the same horsepower requirements can be utilized as in the prior art, and pad formation achieved over a smaller formation zone than in the prior art equipment to thereby permit the use of equipment which occupies less plant space.

What is claimed is:

1. A method for forming a fibrous pad by employing a forming member including a cavity having a foraminous forming surface and upper margins defining an opening into said cavity, the area of the foraminous forming surface being greater than the area of the opening bound by the upper margins of said cavity, said method comprising the steps of:

A. forming a gaseous suspension of fibers;
   B. establishing a pressure drop across the foraminous forming surface of the cavity to direct the gas of the suspension through the forming surface, and to condense the fibers of the suspension onto the forming surface in the form of a fibrous layer incompletely filling said cavity;
   C. directing a transfer conveyor into overlying relationship with, and closely adjacent to the orfice of the cavity after the fibrous layer is formed in said cavity; and
   D. transferring the fibrous layer to said transfer conveyor and confining said fibrous layer to a lesser area on the transfer conveyor than it occupied on the foraminous forming surface to form a fibrous pad having a greater basis weight than that of the fibrous layer on the foraminous forming surface.

2. The method according to claim 1, wherein allegiance of the layer is transferred from the cavity to the transfer conveyer by terminating the pressure drop across the foraminous forming surface of the cavity, and establishing a pressure drop across the transfer conveyor while the pressure drop across the forming surface is terminated.

* * * * *